United States Patent
Kim et al.

(10) Patent No.: US 9,678,124 B2
(45) Date of Patent: Jun. 13, 2017

(54) PHASE MEASUREMENT DEVICE AND METHOD IN MICROWAVE TOMOGRAPHY SYSTEM

(71) Applicant: Electronics and Telecommunications Research Institute, Daejeon (KR)

(72) Inventors: Hyuk-Je Kim, Daejeon (KR); Jong-Moon Lee, Cheongju-si (KR); Seong-Ho Son, Daejeon (KR); Soon-Ik Jeon, Daejeon (KR); Hyung-Do Choi, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 252 days.

(21) Appl. No.: 14/496,447

(22) Filed: Sep. 25, 2014

(65) Prior Publication Data

US 2015/0084644 A1    Mar. 26, 2015

(30) Foreign Application Priority Data

Sep. 26, 2013  (KR) .......................... 10-2013-0114590

(51) Int. Cl.
   *G01R 25/00*    (2006.01)
   *G01N 22/00*    (2006.01)

(52) U.S. Cl.
   CPC ............. *G01R 25/00* (2013.01); *G01N 22/00* (2013.01)

(58) Field of Classification Search
   USPC ............ 324/605, 637–642; 600/430; 342/53
   See application file for complete search history.

(56) References Cited

U.S. PATENT DOCUMENTS

| | | | |
|---|---|---|---|
| 5,751,830 A * | 5/1998 | Hutchinson | G01S 17/89 342/53 |
| 6,448,788 B1 | 9/2002 | Meaney et al. | |
| 6,841,997 B2 | 1/2005 | Feiweier | |
| 2004/0077943 A1* | 4/2004 | Meaney | A61B 5/05 600/430 |
| 2010/0150467 A1 | 6/2010 | Zhao et al. | |

FOREIGN PATENT DOCUMENTS

EP         2287632 A1     2/2011
KR    1020020086289 A    11/2002

\* cited by examiner

*Primary Examiner* — Vincent Q Nguyen
(74) *Attorney, Agent, or Firm* — William Park & Associates Ltd.

(57) ABSTRACT

A phase measurement method in a microwave tomography system may include transmitting a first Tx frequency signal, receiving a signal corresponding to the first Tx frequency signal, and measuring a first phase value; transmitting a second Tx frequency signal separated by a predetermined discrete frequency from the first Tx frequency signal, receiving a signal corresponding to the second Tx frequency signal, and measuring a second phase value; calculating a first phase difference based on a difference between the first and second phase values; calculating a second phase difference based on the discrete frequency; and determining an unwrapped phase value through comparison between the first and second phase differences.

5 Claims, 3 Drawing Sheets

PHASE MEASUREMENT DEVICE AND METHOD IN MICROWAVE TOMOGRAPHY SYSTEM

CROSS-REFERENCE TO RELATED APPLICATIONS

The present application claims priority of Korean Patent Application No. 10-2013-0114590, filed on Sep. 26, 2013, which is incorporated herein by reference in its entirety.

BACKGROUND OF THE INVENTION

Field of the Invention

Exemplary embodiments of the present invention relate to a microwave tomography system; and, more particularly, to a phase measurement device and method in a microwave tomography system.

Description of Related Art

A microwave tomography system emits a microwave signal onto a measurement target, measures the magnitude and phase value of a scattered microwave signal, and analyzes inverse scattering using the measured magnitude and phase value of the microwave signal. Through this operation, the microwave tomography system can calculate internal permittivity and conductivity of the measurement target. Thus, the microwave tomography system can perform nondestructive inspection for the inside of the measurement target. The phase value of the scattered microwave, measured through the microwave tomography system, must be an unwrapped phase value. However, when the measured phase value is a wrapped phase value, a result value obtained through the inverse scattering analysis may diverge or the precision of the analysis may decrease. For example, when the unwrapped phase value of the scattered microwave signal is 400 degrees, the phase value may be expressed as a wrapped phase value of 40 degrees (400 degrees-360 degrees). In this case, when the inverse scattering analysis is performed through the wrapped phase value of 40 degrees, the result value may diverge or become incorrect.

The microwave tomography system may acquire phase-unwrapped data through the following method. The microwave tomography system emits microwave signals onto a measurement target at various frequencies from a low frequency to a high frequency at a predetermined interval, receives scattered microwave signals, compares phase values measured at the low frequency and the high frequency, respectively, and determines whether the measured phase values are unwrapped values.

According to the method for acquiring unwrapped data in the microwave tomography system, the phase value at the initial low frequency must not be unwrapped. Furthermore, in order to find a phase value at the high frequency, the microwave tomography system must measure phase values while sequentially changing the frequency from the phase value at the low frequency. Thus, the microwave tomography system must have a function of transmitting/receiving wideband microwave signals.

The microwave tomography system must change the frequency from the low frequency to the high frequency. Thus, the measurement time and the cost required for constructing the system are inevitably increased.

SUMMARY OF THE INVENTION

An embodiment of the present invention is directed to a phase measurement device capable of achieving narrowband microwave transmission/reception in a microwave tomography system.

Another embodiment of the present invention is directed to a phase measurement device capable of reducing a measurement time and a manufacturing cost in a microwave tomography system.

Another embodiment of the present invention is directed to a phase measurement device capable of increasing resolution by increasing a measurement frequency band in a microwave tomography system.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an embodiment of the present invention, a phase measurement device in a microwave tomography system may include: a transmit (Tx) frequency generator configured to generate a first frequency signal and a second frequency signal separated by a predetermined discrete frequency from the first frequency signal; a local oscillation frequency generator configured to generate a first local oscillation frequency signal separated by an intermediate frequency from the first frequency signal and a second local oscillation frequency signal separated by the intermediate frequency from the second frequency signal; a low noise amplifier (LNA) configured to receive a third frequency signal corresponding to the first frequency signal and a fourth frequency signal corresponding to the second frequency signal, low-noise-amplify the received signals, and output the amplified signals; a mixer configured to generate a first mixed signal by mixing the third frequency signal and the first local oscillation frequency signal, and generate a second mixed signal by mixing the fourth frequency signal and the second local oscillation frequency signal; an intermediate frequency (IF) filter configured to generate a first IF signal obtained by filtering an IF band from the first mixed signal, and generate a second IF signal obtained by filtering the IF band from the second mixed signal; a phase measurement unit configured to measure a first phase value from the first IF signal, and measure a second phase value from the second IF signal; and an unwrapped phase calculation unit configured to determine an unwrapped phase value based on a first phase difference calculated from a difference between the first and second phase values and a second phase difference corresponding to the discrete frequency.

In accordance with another embodiment of the present invention, a phase measurement method in a microwave tomography system may include: transmitting a first Tx frequency signal, receiving a signal corresponding to the first Tx frequency signal, and measuring a first phase value; transmitting a second Tx frequency signal separated by a predetermined discrete frequency from the first Tx frequency signal, receiving a signal corresponding to the second Tx frequency signal, and measuring a second phase value; calculating a first phase difference based on a difference between the first and second phase values; calculating a second phase difference based on the discrete frequency; and determining an unwrapped phase value through comparison between the first and second phase differences.

DESCRIPTION OF SPECIFIC EMBODIMENTS

Figure 1:
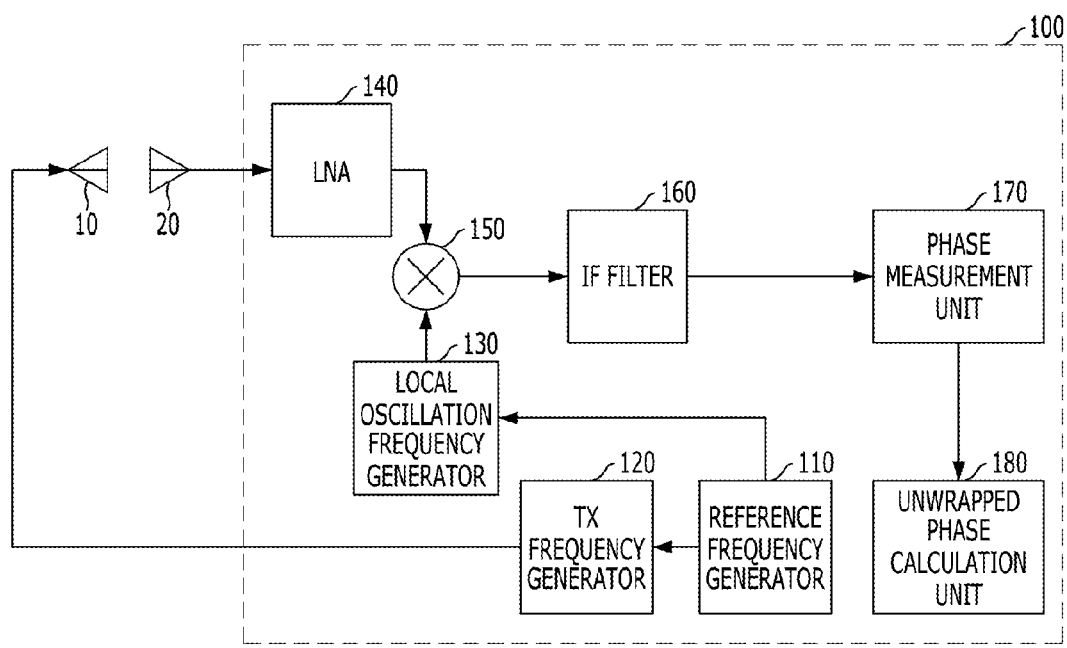
FIG. 1 schematically illustrates the structure of a phase measurement device in accordance with an embodiment of the present invention.

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Throughout the disclosure, like reference numerals refer to like parts throughout the various figures and embodiments of the present invention.

An exemplary embodiment of the present invention provides a phase measurement device with a narrowband microwave transmitting/receiving function in a microwave tomography system. The phase measurement device in accordance with the embodiment of the present invention may measure am unwrapped phase value using a discrete frequency between two frequency signals. In the embodiment of the present invention, the phase measurement device applied to the microwave tomography system will be described. However, the phase measurement device in accordance with the embodiment of the present invention may also be applied to other measurement systems for measuring a measurement target, in addition to the microwave tomography system.

FIG. 1 schematically illustrates the structure of a phase measurement device in accordance with an embodiment of the present invention.

Referring to FIG. 1, the phase measurement device 100 includes a reference frequency generator 110, a transmit (Tx) frequency generator 120, a local oscillation frequency generator 130, a low noise amplifier (LNA) 140, a mixer 150, an intermediate frequency (IF) filter 160, a phase measurement unit 170, and an unwrapped phase calculation unit 180.

The phase measurement device 100 may be connected to a Tx antenna 10 and a receive (Rx) antenna 20. In the following descriptions, suppose that the phase measurement device 100 includes the Tx antenna 10 and the Rx antenna 20.

The reference frequency generator 110 generates a reference frequency signal. Furthermore, the reference frequency generator 110 outputs the reference frequency signal to the Tx frequency generator 120 and the local oscillation frequency generator 130.

The Tx frequency generator 120 generates a Tx frequency signal using the reference frequency signal. The Tx frequency generator 120 is connected to the Tx antenna 10, and emits the Tx frequency signal through the Tx antenna 10.

The local oscillation frequency generator 130 generates a local oscillation frequency signal using the reference frequency signal. The local oscillation frequency generator 130 outputs the generated local oscillation frequency signal to the mixer 150.

The signal emitted through the Tx antenna 10 may be received through the Rx antenna 20. At this time, a measurement target may be positioned between the Tx antenna 10 and the Rx antenna 20.

The LNA 140 is connected to the Rx antenna 20, and amplifies the signal received through the Rx antenna 20, while suppressing noise contained in the received signal. The LNA 140 outputs the amplified frequency signal to the mixer 150.

The mixer 150 mixes the local oscillation frequency signal generated through the local oscillation frequency generator 130 with the frequency signal amplified through the LNA 120. The mixer 150 outputs the mixed signal to the IF filter 160.

The IF filter 160 filters only signals in an IF band from the mixed signal. The IF filter 160 outputs the filtered IF signal to the phase measurement unit 170.

The phase measurement unit 170 measures a phase value from the filtered signal. The measured phase value may range from −180 degrees to +180 degrees. Furthermore, the phase measurement unit 170 may measure the magnitude of the signal. The phase measurement unit 170 outputs the measured phase value of the signal to the unwrapped phase calculation unit 180.

The unwrapped phase calculation unit 180 calculates an unwrapped phase value using the received phase values.

The operation of the phase measurement device in accordance with the embodiment of the present invention will be briefly described as follows.

The Tx frequency generator 120 in accordance with the embodiment of the present invention generates two frequency signals (first and second frequency signals) separated by a predetermined discrete frequency.

At this time, the phase measurement unit 170 measures a first phase value from a first IF signal received through transmission of the first frequency signal. Then, the phase measurement unit 170 measures a second phase value from a second IF signal received through transmission of the second frequency signal.

The unwrapped phase calculation unit 180 may divide data into unwrapped data and wrapped data through a comparison between the first and second phase values. Through this operation, the unwrapped phase calculation unit 180 may determine an unwrapped phase value through the divided data.

The operations of the phase measurement unit 170 and the unwrapped phase calculation unit 180 will be described in detail with reference to FIG. 3.

The phase measurement device 100 in accordance with the embodiment of the present invention may determine an unwrapped phase value using only two frequency signals having a predetermined discrete frequency. Thus, the phase measurement device 100 does not need to generate wideband frequency signals and a plurality of frequency signals having a predetermined interval. Thus, the phase measurement device 100 in accordance with the embodiment of the present invention may achieve narrowband microwave transmission/reception.

Figure 2:
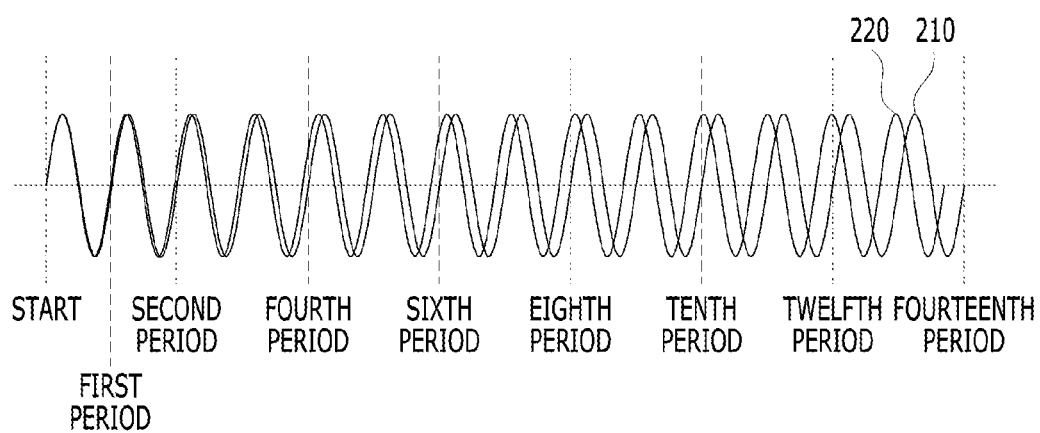
FIG. 2 is a diagram schematically illustrating changes based on the distance between two signals of which the frequencies are separated from each other, in accordance with the embodiment of the present invention.

FIG. 2 is a diagram schematically illustrating changes based on the distance between two signals of which the frequencies are separated from each other, in accordance with the embodiment of the present invention.

FIG. 2 illustrates the states of two frequency signals 210 and 220 of which the frequencies are separated from each other, based on the changes of distance. The first frequency signal 210 and the second frequency signal 220 are separated from each other.

The first and second frequency signals 210 and 220 are continuous wave (CW) signals between which a discrete frequency is very small. As the moving distance increases, the phase difference between the two frequency signals 210 and 220 increases. For example, the increase of the phase difference may be checked through a phase difference between the frequency signals at a first period and a phase difference between the frequency signals at a 14th period.

When the discrete frequency +between the two frequency signals 210 and 220 is checked, a phase difference between the two frequency signals 210 and 220 after the first period may be checked.

Figure 3:
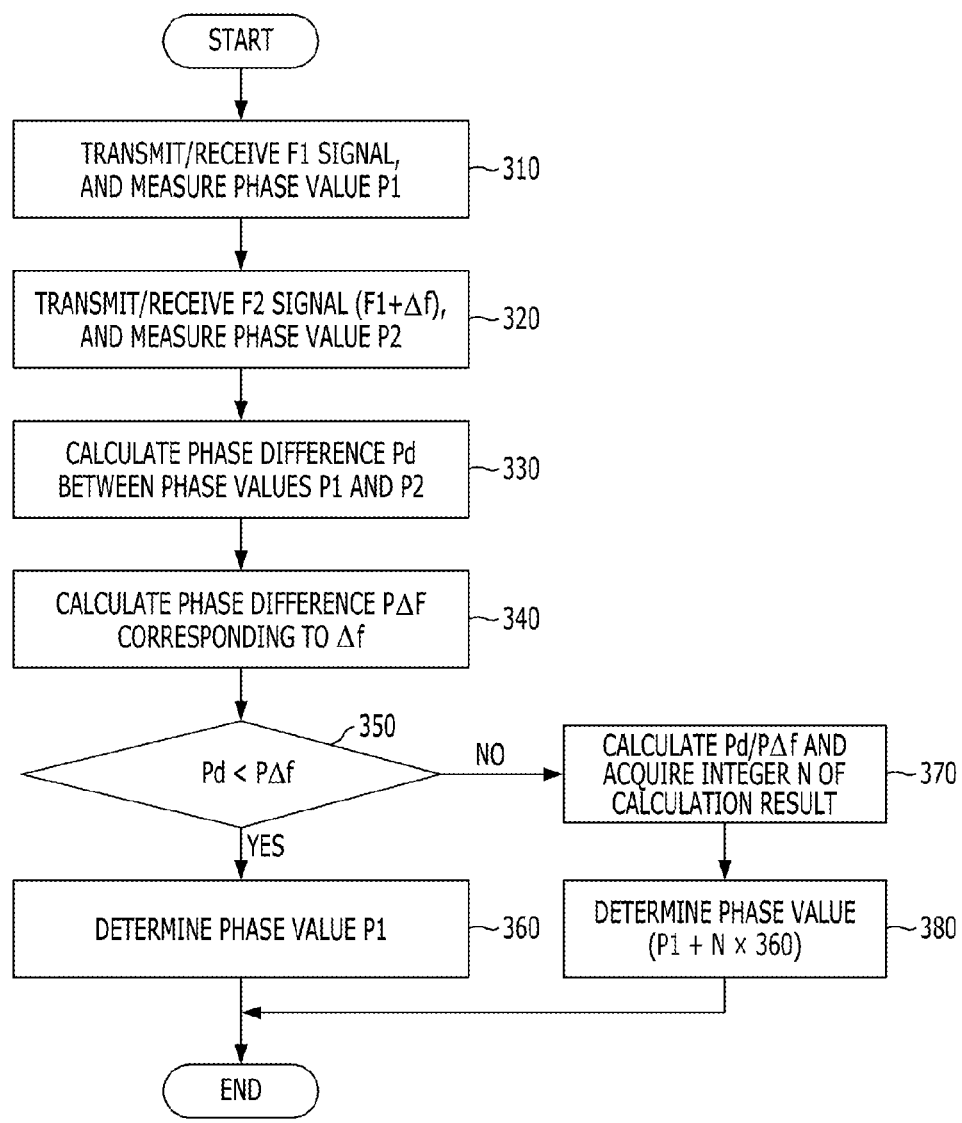
FIG. 3 is a diagram schematically illustrating the operation of the phase measurement device in accordance with the embodiment of the present invention.

FIG. 3 is a diagram schematically illustrating the operation of the phase measurement device in accordance with the embodiment of the present invention.

Referring to FIG. 3, the phase measurement unit 170 receives a first IF signal based on a first frequency signal F1 generated through the Tx frequency generator 120, and measures a first phase value P1 using the received first IF signal, at step S310. The phase measurement unit 170 outputs the first phase value P1 to the unwrapped phase calculation unit 180.

At step S320, the phase measurement unit 170 receives a second IF signal based on a second frequency signal F2 generated through the Tx frequency generator 120, and measures a second phase value P2 using the received second IF signal. The second frequency signal F2 has a frequency (F1+Δf) separated by a discrete frequency Δf from the first frequency. The phase measurement unit 170 outputs the second phase value P2 to the unwrapped phase calculation unit 180.

The operations of receiving the first IF signal and the second IF signal at steps S310 and S320, respectively, will be described with reference to FIG. 1.

The Tx frequency generator 120 generates the first frequency signal F1, and emits the first frequency signal F1 through the Tx antenna 10. The local oscillation frequency generator 130 generates a first local oscillation frequency signal. The LNA 140 receives a third frequency signal corresponding to the first frequency signal F1 through the Rx antenna 20. The mixer 150 mixes the first local oscillation frequency signal with the third frequency signal and generates a first mixed signal. The IF filter 160 generates the first IF signal by filtering only signals in an IF band from the first mixed signal.

Then, the Tx frequency generator 120 generates a second frequency signal F2, and emits the second frequency signal F2 through the Tx antenna 10. The local oscillation frequency generator 130 generates a second local oscillation frequency signal. The LNA 140 receives a fourth frequency signal corresponding to the second frequency signal F2 through the Rx antenna 20. The mixer 150 mixes the second local oscillation frequency signal and the fourth frequency signal and generates a second mixed signal. The IF filter 160 generates the second IF signal by filtering only signals in the IF band from the second mixed signal.

At step S330, the unwrapped phase calculation unit 180 calculates a first phase difference Pd between the first and second phase values P1 and P2.

At step S340, the unwrapped phase calculation unit 180 calculates a second phase difference PΔf corresponding to the discrete frequency Δf.

At step S350, the unwrapped phase calculation unit 180 compares the first phase difference Pd acquired from the received signals to the second phase difference PΔf corresponding to the discrete frequency Δf.

When it is determined at step S350 that the first phase difference Pd is smaller than the second phase difference PΔf, the operation proceeds to step S360. At this time, the measured first phase value P1 may indicate that the signal exists within one period of the frequency, and include unwrapped data.

At step S360, the unwrapped phase calculation unit 180 determines the first phase value P1 as the unwrapped phase value, and ends the operation.

When it is determined at step S350 that the first phase difference Pd is not smaller than the second phase difference PΔf, the operation proceeds to step S370. At this time, the measured first phase value P1 is wrapped data.

At step S370, the unwrapped phase calculation unit 180 divides the first phase difference Pd by the second phase difference PΔf (Pd/PΔf), and acquires only an integer value N from the result obtained through the division. The unwrapped phase calculation unit 180 may determine how many periods the frequency has passed through, from the acquired integer value N.

At step S380, the unwrapped phase calculation unit 180 multiplies the integer value N by 360. Then, the unwrapped phase calculation unit 180 determines an unwrapped phase value by adding the multiplication result to the first phase value P1, and ends the operation. The operation of the unwrapped phase calculation unit 180 may be expressed as Equation 1 below.

$$P1+N*360 \qquad \text{[Equation 1]}$$

For example, when an unwrapped phase value at 5 GHz is sought, the unwrapped phase calculation unit 180 uses a first frequency signal of 5 GHz and a second frequency signal of 5.1 GHz, which has a discrete frequency Δf of 100 MHz from the first frequency signal. The phase measurement unit 170 measures a first phase value P1 through the first frequency signal F1, and measures a second phase value P2 through the second frequency signal F2.

At this time, a second phase difference PΔf between the first and second frequency signals F1 and F2 at the period of 5 GHz is calculated as 7.2 degrees (360 degrees*(100 MHz/5 GHz)) per one period.

Thus, when the first phase difference Pd between the first and second phase values P1 and P2 is smaller than 7.2 degrees, the unwrapped phase calculation unit 180 determines the first phase value P1 as an unwrapped phase value. On the other hand, when the first phase difference Pd is not smaller than 7.2 degrees, the unwrapped phase calculation unit 180 acquires an integer value N by dividing the first phase difference Pd by 7.2. Then, the phase unwrapped calculation unit 180 determines an unwrapped phase value using the acquired integer value N, based on Equation 1.

The phase measurement device 100 in accordance with the embodiment of the present invention may achieve narrowband microwave transmission/reception, and reduce the measurement time required for the measurement target positioned between the Tx antenna and the Rx antenna and the manufacturing cost of the phase measurement device. Furthermore, the phase measurement device 100 in accordance with the embodiment of the present invention may increase the measurement frequency band, thereby increasing the resolution.

In accordance with the embodiments of the present invention, the phase measurement device may determine an unwrapped phase value using only two frequency signals having a predetermined discrete frequency, and achieve narrowband microwave transmission/reception. Furthermore, since the phase measurement device uses only two frequency signals, the phase measurement device may reduce the measurement time required for the measurement target and the manufacturing cost thereof. Furthermore, the phase measurement device may increase the resolution by increasing the measurement frequency band.

While the present invention has been described with respect to the specific embodiments, it will be apparent to those skilled in the art that various changes and modifications may be made without departing from the spirit and scope of the invention as defined in the following claims.

What is claimed is:

1. A phase measurement device in a microwave tomography system, comprising:
    a reference frequency generator configured to generate a reference frequency signal;
    a transmit (Tx) frequency generator configured to generate a first continuous wave frequency signal using the reference frequency signal and to generate a second continuous wave frequency signal using the reference frequency signal, the first continuous wave frequency signal and the second continuous wave frequency signal being separated by a predetermined frequency amount and further configured to transmit from a transmit antenna the first continuous wave frequency signal and the second continuous wave frequency signal;
    a local oscillation frequency generator that receives the reference frequency signal from the reference frequency generator and is configured to generate a first local oscillation frequency signal using the reference signal and is configured to generate a second local oscillation frequency signal using the reference signal, the second local oscillation frequency signal being separated from the second continuous wave frequency signal by a predetermined intermediate frequency amount;
    a low noise amplifier (LNA) configured to receive from a receive antenna a first receive frequency signal corresponding to the first continuous wave frequency signal and a second receive frequency signal corresponding to the second continuous wave frequency signal, to low-noise-amplify the first receive frequency signal and the second receive frequency signal, and to output a respective amplified first receive frequency signal and amplified second receive frequency signal;
    a mixer configured to generate a first mixed signal by mixing the amplified first receive frequency signal and the first local oscillation frequency signal, and generate a second mixed signal by mixing the amplified second receive frequency signal and the second local oscillation frequency signal;
    an intermediate frequency (IF) filter configured to generate a first IF signal obtained by filtering an IF band from the first mixed signal, and generate a second IF signal obtained by filtering the IF band from the second mixed signal;
    a phase measurement unit configured to measure a first phase value from the first IF signal, and measure a second phase value from the second IF signal; and
    an unwrapped phase calculation unit configured to determine an unwrapped phase value based on a first phase difference calculated from a difference between the first and second phase values and a second phase difference corresponding to the discrete frequency.

2. The phase measurement device of claim 1, wherein the unwrapped phase calculation unit determines the first phase value as the unwrapped phase value, when the first phase difference is smaller than the second phase value.

3. The phase measurement device of claim 1, wherein when the first phase difference is not smaller than the second phase difference, the unwrapped phase calculation unit corrects the first phase value using an elapsed period between the first and second continuous wave frequency signals, and determines the corrected first phase value as the unwrapped phase value.

4. The phase measurement device of claim 3, wherein the elapsed period comprises an integer value obtained by dividing the first phase difference by the second phase difference.

5. The phase measurement device of claim 4, wherein the unwrapped phase calculation unit multiplies the integer value by 360, adds the multiplication result and the first phase value, and determines the addition result as the unwrapped phase value.

* * * * *